United States Patent [19]

Cerami et al.

[11] 4,424,216

[45] Jan. 3, 1984

[54] METHOD FOR THE REDUCTION OF MUCIN VISCOSITY

[75] Inventors: Anthony Cerami, Flanders, N.J.; Nina F. Tabachnik, Little Neck, N.Y.

[73] Assignee: The Rockefeller University, New York, N.Y.

[21] Appl. No.: 62,503

[22] Filed: Jul. 31, 1979

[51] Int. Cl.$^3$ .................... A01N 31/66; A01N 31/15; A01N 31/44; A01N 31/47
[52] U.S. Cl. .................................. 424/211; 424/128; 424/224; 424/258; 424/263; 424/326; 424/336; 546/300; 546/162
[58] Field of Search ............... 424/211, 326, 336, 128, 424/258, 263, 224

[56] References Cited

U.S. PATENT DOCUMENTS 3,892,824  7/1975  Piper et al. ........................... 424/211

OTHER PUBLICATIONS

"Studies on the Reduction of Sputum Viscosity in Cystic Fibrosis Using an Orally Absorbed Protected Thiol", Tabachnik, Peterson, and Cerami, Apr. 22, 1980; vol. 214, No. 2; pp. 246–249.

"Protein Binding of N-2-Mercaptoethyl-1,3-Diaminopropane via Mixed Disulfide Formation after Oral Administration of WR 2721[1]", Tabachnik, Blackburn, Peterson and Cerami; vol. 220, No. 2; Oct. 19, 1981; pp. 243–246.

"Biochemical and Rheological Characterization of Sputum Mucins from a Patient with Cystic Fibrosis", Tabachnik, Blackburn, and Cerami; vol. 256, No. 14; Jul. 25, 1981, pp. 7161–7165.

Survey of Compounds which have been Tested for Carcinogenic Activity, pp. 21,23,113,153,154,469; Thompson and Co., Publishers, DHEW Pub. No. (NIH)72-35 (1968–1969 volume).

Primary Examiner—Alan L. Rotman
Attorney, Agent, or Firm—Oblon, Fisher, Spivak, McClelland & Maier

[57] ABSTRACT

A method for reducing mucin viscosity which comprises administering an effective dose of a compound having protected sulfhydryl groups which metabolize in vivo to produce free sulfhydryl groups.

8 Claims, 3 Drawing Figures

METHOD FOR THE REDUCTION OF MUCIN VISCOSITY

BACKGROUND OF THE INVENTION

1. Field of the Invention

The present invention is directed to a method for reducing mucin viscosity in mammals.

2. Description of the Prior Art

The prior art techniques for treating mucus conditions have depended upon where the mucus was located in the body. Mucus impaction of the gastrointestinal tract, biliary and pancreatic ducts generally required surgical techniques for its removal since its viscosity was too high for the body to rid itself of the mucus by its normal path. Mucus in the respiratory tract—often called sputum—has been treated by a variety of techniques including cough syrup and the like. One typical technique for respiratory obstructions has involved the aerosolization of N-acetylcysteine. While N-acetylcysteine is very effective in reducing sputum viscosity, it is extremely difficult, if not impossible, to obtain adequate delivery of this agent to the small airways of the lungs. Hence, its effectiveness in reducing the sputum viscosity is variable depending upon whether or not adequate delivery has been attained. In addition, N-acetylcysteine is extremely irritating to gastrointestinal and respiratory mucosa.

The problem of elevated sputum viscosity is particularly aggravated in those individuals suffering from cystic fibrosis wherein the high viscosity of the sputum leads to clinical difficulties in clearance of the respiratory and gastrointestinal tracts and in delivery of gas and nutrients to their respective sites. Furthermore, in newborns, the cystic fibrosis may be present as meconium ileus, an intestinal obstructive syndrome due to the secretion of abnormally viscid gastrointestinal mucus. At the present time, the only method of treating these intestinal obstructions is through surgical techniques to physically remove the blockage.

Accordingly, there exists a need for a method of treating mucus impactions and for the reduction of sputum viscosity which does not involve either surgical intervention or the delivery of drugs in aerosol form.

SUMMARY OF THE INVENTION

Accordingly, it is an object of the present invention to provide a treatment technique which provides for the reduction in the viscosity of mucin solutions.

It is a further object of the present invention to provide a treatment for respiratory and gastrointestinal obstructions through the reduction of sputum and mucus viscosities.

It is yet another object of the present invention to achieve the reduction of sputum viscosity by a treatment involving either the oral or intravenous injection of a drug into the mammal.

These and other objects of the present invention which will become apparent have been attained through the oral or intravenous administration of a compound which is metabolized in vivo to produce compounds containing sulfhydryl groups.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DESCRIPTION OF THE PREFERRED EMBODIMENTS

Figure 1:
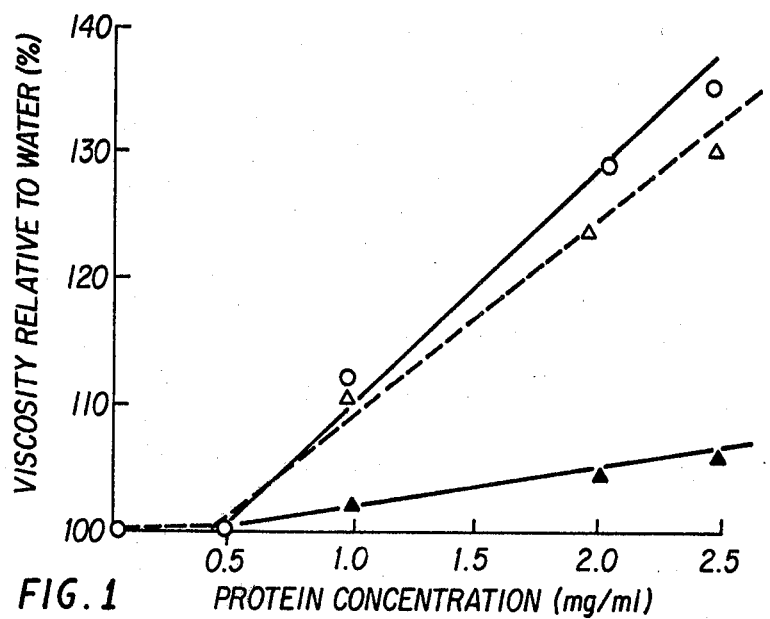
FIG. 1 demonstrates the change in viscosity of component I (Δ—Δ—Δ), Component IA (O—O—O), whole sputum (●-●-●-●), and fibrinogen ( ▲-▲ ▲ ) with protein concentration (A)

The present invention is based on the isolation of a mucin having a high molecular weight of 425,000 D from the sputum of a patient with cystic fibrosis. This protein may be responsible for the increased viscosity of the sputum since increasing its concentration results in a rise in viscosity. Also, as in the case of the crude sputum, the viscosity of the purified mucin can be decreased by treatment with sulfhydryl reducing agents. Similar results were also obtained with sputum obtained from patients suffering from pneumuccocal pneumonia, chronic bronchitis and the like. The biochemical effect of the reducing agents on sputum mucin viscosity is to split the molecule into a component which retains most of the carbohydrate and at least two small peptides having molecular weights of 65,000 Daltons and 27,000 Daltons. This structural change leads to a dramatic alteration of the rheological properties of the molecule. This alteration of the rheological properties of the molecule would allow the body to rid itself of the mucus secretions via the normal body processes. Although we did find the use of sulfhydryl compounds to be very effective in reducing the mucus viscosity, the administration of sulfhydryl compounds to mammals has not proven to be a satisfactory method for treating mucin with sulfhydryl compounds to be administered either intravenously or orally. In particular, fairly large doses of the sulfhydryl compound must be given to compensate for the reaction of the free thiol with plasma and gastrointestinal proteins while enroute to the lungs and other organs where mucus impaction may have occurred. At the dosages which must be given, the sulfhydryl compounds can lead to toxic side effects. We have now discovered the problem which we encountered with the administration of sulfhydryl compounds to reduce mucin viscosity may be overcome by administering the compounds which are converted to sulfhydryl groups in vivo. Suitable compounds include pharmaceutically acceptable thiosulfates, thiophosphates, disulfides and the like. The compounds which are suitable for use in the present invention are all characterized by containing a blocked sulfhydryl group wherein the blocking agent is removed in vivo to form a sulfhydryl group. Suitable compounds include aminoalkylthiosulfuric acids, aminoalkylphosphorothioates, thiosulfatoalkylamines, phenalkylaminoalkylthiosulfuric acids, hydroxyalkylaminoalkylthiosulfuric acids, hydroxyaminoalkylphosphorothioates, alkoxyalkylaminoalkylthiosulfuric acids, cycloalkyloxyaminoalkylthiosulfuric acids, phenoxyalkylaminoalkylthiosulfuric acids, cycloalkylaminoalkylthiosulfuric acids, cycloalkylalkylaminoalkylphosphorothioates, cycloalkylalkylaminoalkyldisulfides, phenoxyalkylaminoethyldisulfides, hydroxyalkylaminoalkyldisulfides, alkylamidiniumthiosulfates, acetamidine derivatives containing a blocked sulfhydryl group, arylalkylamidiniumthiosulfates, aminoalkylaminoalkylphosphorothioates, quinolyloxyalkylaminoalkylthiosulfuric acids, pyridyloxyalkylaminoalkylthiosulfuric acids, phenoxy- and phenylthioalkylamidiniumthiosulfates, cycloalkylamidiniumthiosulfates, and the like. In general, any compound containing a blocked sulfhydryl group which is pharmaceutically acceptable may be employed in the present invention provided its blocked sulfhydryl group is converted to the free sulfhydryl group in vivo.

The following compounds are preferred for use in the present invention:
1. $(H_2NCOCH_2CH_2NHCH_2CH_2S-)_2$
2. $H_2NCOCH_2CH_2NHCH_2CH_2SSO_3H$
3. $H_2NCOCH_2CH_2NHCH_2CH_2SPO_3H_2$
4. $H_2N(CH_2)_3NHCH_2CH_2SSO_3H$
5. $(H_2N(CH_2)_3NHCH_2CH_2S-)_2$
6. $CH_3(CH_2)_9NHCH_2CH_2SSO_3H$
7. $CH_3(CH_2)_9NHCH_2CH_2SPO_3H_2$
8. $(CH_3(CH_2)_9NHCH_2CH_2S-)_2$
9. $H_2NCH_2CH_2SPO_3H_2$
10. $H_2N(CH_2)_5NH(CH_2)_2SPO_3H_2$
11. $H_2N(CH_2)_3NH(CH_2)SPO_3H_2$ Of these compounds, (11) is particularly preferred. This compound has been designated WR 2721 in toxological tests conducted at the Walter Reed Army Medical Center. This compound has been proposed as a novel antiradiation drug and is the subject of U.S. Pat. No. 3,892,824.

In the treatment of the present invention, the compound containing the blocked sulfhydryl group is administered to the patient at a dosage rate sufficient to reduce the mucin viscosity. Dosage rates ranging from 1 mg/kg/day to an excess of 100 mg/kg/day have proven satisfactory. Dosage rates in the order of from 5 to 50 mg/kg/day are preferably employed. A particularly preferred dosage rate involves the administration of 5 mg/kg four times a day. The compound may be administered either orally or intravenously in conjunction with a suitable pharmaceutical carrier. Intravenous administration may involve the use of physiological saline solutions which may or may not contain a sodium carboxy methyl cellulose and if desired TWEEN 80 ®. Obviously, simple physiological saline solutions may be employed; water alone can be used, or the like.

In the preferred method the compound is administered orally with a suitable solid carrier. If desired, adjuvants such as buffers and the like may be employed. It may be embodied in suitable tablet form, such as a WR 2721 containing tablet provided with an enteric coating, MR 2721 being present in major or minor amount. It may also be administered in a suitable capsule, of gelatin or the like.

U.S. Pat. No. 3,892,824 reports on the toxicity of the compound falling within formula I above. Animal studies conducted on these compounds revealed LD 50's ranging from 450 mg/kg up to 1,300 mg/kg. For the compound identified as WR 2721 no toxicity problems were encountered at regular doses of up to 100 mg/kg/day in these toxological tests. In tests on WR 2721 for its possible side effects, dosages were given to human volunteers at rates of up to 30 mg/kg/day without any adverse effects being noted. For this reason compound WR 2721 is the preferred compound in view of the extensive pharmaceutical tests in connection with its use as an antiradiation drug which have been performed to date.

Having generally described this invention, a further understanding can be obtained by reference to certain specific examples which are provided herein for purposes of illustration only and are not intended to be limiting unless otherwise specified.

EXAMPLE 1

In the following examples, the following abbreviations have been used:
GSSG—reduced glutathione
GSH—oxidized glutathione
SDS—sodium dodecyl sulphate
DTE—dithioerythritol
DMS—dimercaptosuccinic acid
MDP—N-2-mercaptoethyl-1,3-diaminopropane MDP was prepared by boiling WR 2721 in 1 M HCl under nitrogen for five minutes. The solution was neutralized with sodium bicarbonate.

Sputa were obtained by postural drainage from a 7-year old male patient with a confirmed diagnosis of cystic fibrosis.

Samples were collected in jar containing 0.5 ml of injectable gentamycin sulfate. Upon receipt the samples were added to 0.1 ml of a 1 M sodium azide solution and processed within 24 hours of collection.

Isolation and Electrophoretic Characterization of Sputum Components:

A 10-ml aliquot of whole cystic fibrosis sputum was applied to a column (4×70 cm) of Biogel A5M (BioRad Corporation, Richmond, CA) equilibrated with 0.01 M phosphate buffer (pH 7.0) containing 0.1 M NaCl and 1 mM sodium azide and eluted with the same buffer. The material appearing in the void volume was pooled and designated component I.

After isolation on Biogel A5M, component I was passed successively through 0.8, 0.5 and 0.22μ filters (Millipore Corporation, Bedford, MA) to eliminate any possible bacterial contamination.

Component I was concentrated to 5 ml by volume dialysis in tubing of ⅜" diameter (SGA Scientific, Bloomfield, NJ) and added to a final concentration of 4% SDS. This sample was washed through an Amicon XM100A filter (Amicon, Lexington, MA) under $N_2$ pressure with 500 ml of 0.01 M phosphate buffer (pH 7.0) containing 0.1 M NaCl and 4% SDS. The material retained by the filter was designated component IA and was reconcentrated by vacuum dialysis for use in subsequent experiments.

SDS-Polyacrylamide gradient gel electrophoresis (5-16% acrylamide) was performed by the method of Maizel, J. V. (1971) Methods Virol. 5:179-246. Gels were stained with either Coomassie blue; Fairbanks, G., T. L. Steck, D. F. H. Wallach, (1971) Biochem. 10:2606-2617; or periodic acid-Schiff reagent; Zacharias, R. J., T. E. Zell, J. H. Morrison, J. J. Woodlock, (1969) Anal. Biochem. 31:148-152.

Purification and Characterization of Component IA:
SDS-polyacrylamide gel electrophoresis was performed on component IA. The major constituent of component IA has an apparent molecular weight of 425

KD. A number of other constituents, one of which (60 KD) is the main contaminant, remain after the Amicon-SDS diafiltration. Efforts to remove these contaminants have not been successful.

Following treatment of component IA with reducing agents gel electrophoresis is revealed several new Coomassie blue staining bands at 65 KD (65,000 Daltons) and 27 KD. These peptides were apparently split from the large molecular weight mucin (425 KD) since PAS staining of another gel revealed a PAS positive band in the same area as the original mucin.

Viscometry:

The viscosity of crude sputum specimens before and after the addition of sulfhydryl agents was measured in a 0.2 ml pipette by determining the time required for 0.08 ml to run out. Purified mucin samples were concentrated by vacuum dialysis and dialyzed against 0.01 M phosphate buffer (pH 7.0) for several days. Their viscosity was then measured using a Beckman Low-Shear Rotary Viscometer (Model 250010). The viscosity of fibrinogen solutions of various concentrations was similarly measured. All viscometric studies were performed at room temperature. Changes in viscosity with the addition of 5 mM DTE were measured by adding 50 λ of a 500 mM aqueous solution of DTE to 5 ml of sample.

Figure 2:
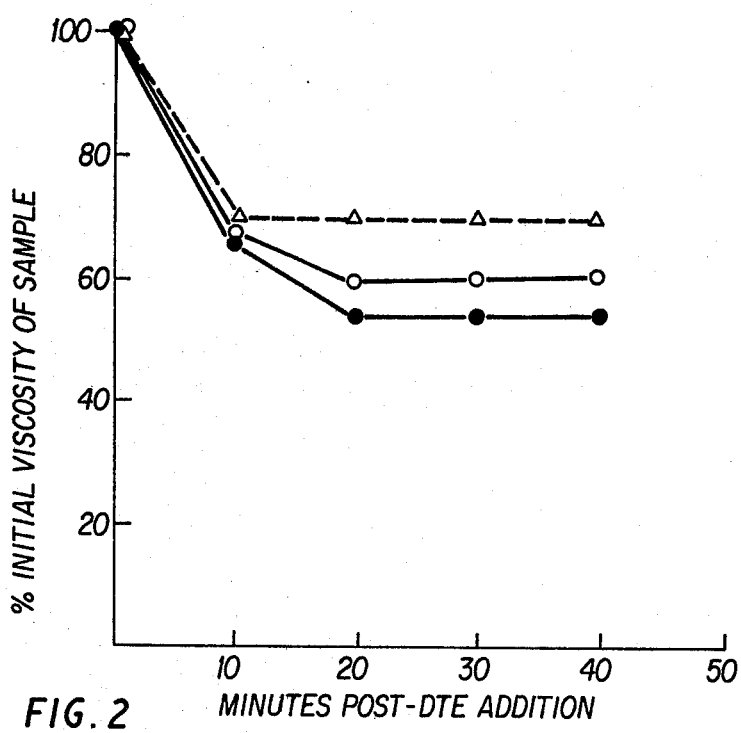
FIG. 2 demonstrates the change in viscosity of components, I, IA and whole sputum with DTE addition (B)

Viscosity of Sputum, Component I and Component IA:

The relationship of protein concentration to viscosity is shown in FIG. 1 for components I, IA and fibrinogen, a large molecular weight glycoprotein. The effect of 5 mM DTE on whole sputum, component I and component IA is shown in FIG. 2. Both purified mucin fractions behave like sputum with respect to viscosity changes upon addition of DTE.

Changes in sputum viscosity upon the addition of various agents are shown in Table I. Of the sulfhydryl compounds tested, DTE was the most efficacious in vitro. The oxidized forms of glutathione and lipoic acid were very much less active than their corresponding thiols, oxidized lipoic acid being totally ineffective in reducing sputum viscosity in vitro. Since DTE might be acting as a metal chelator, and as a result of early reports the high concentration of EDTA could reduce sputum viscosity, nonsulfhydryl chelators were assayed in this system and found to be without effect.

Figure 3:
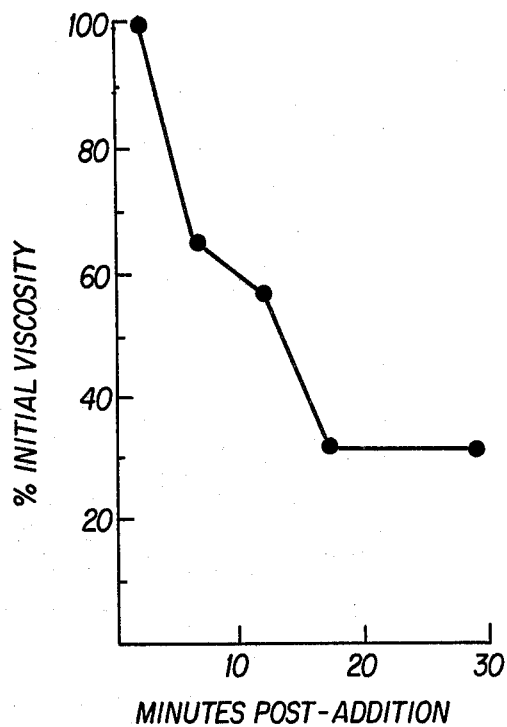
FIG. 3 demonstrates the change in viscosity of whole sputum after addition of 5 mM MDP.

Addition of 5 mM MDP to cystic fibrosis sputum reduced the viscosity by 70% in 15 minutes as shown in FIG. 3. The parent thiophosphate (WR 2721) had no effect on sputum viscosity.

TABLE I

SHORT-TERM VISCOSITY CHANGES OF WHOLE CYSTIC FIBROSIS SPUTUM

| 1 mM Agent Added | Minimum Rel. Viscosity* | Time (min.) |
|---|---|---|
| DTE | 21% | 10 |
| Antabuse | 50% | 10 |
| Dimercaptosuccinate | 50% | 15 |
| GSH | 33% | 40 |
| GSSG | 67% | 15 |
| Lipoate | 100% | 60 |
| Dihydrolipoate | 36% | 10 |
| D-penicillamine | 32% | 20 |
| WR 2721 | 30% | 15 |
| EDTA | 100% | 60 |
| EGTA | 100% | 60 |
| $H_2O_2$ | 100% | 60 |

*Expressed as % of control viscosity.

EXAMPLE 2

Tissue concentrations of MDP were determined at various times after intraperitoneal and oral administration of WR 2721 to mice. Lung and liver homogenates obtained by 5 minutes of hand douncing in 1 ml saline, or 1 mm thick tissue slices, were incubated with 1 mg/ml of WR 2721 at 37° C. Aliquots were taken at various times for assessment of conversion to MDP. Blood was obtained by retro-orbital puncture, the mice sacrificed with $CO_2$, and the lungs removed. The lung and liver homogenates (0.9% in saline w/v) and blood samples were treated with trichloroacetic acid to a final concentration of 10%, and allowed to stand at 4° C. for ten minutes. Samples were centrifuged at 3000 rpm for ten minutes and the supernatant neutralized with sodium bicarbonate. These neutralized supernatants were assayed for the presence of sulfhydryl groups by the method of Ellman et al, (1959) Arch. Biochem. Biophys. 82:70–77.

Metabolic Studies of WR 2721:

WR 2421 appears in the blood of mice as the free thiol after both oral and i.p. administration. The kinetics of appearance of MDP in the lungs of mice are similar to those for blood after oral (not shown) and i.p. administration.

Oral administration of WR 2721 leads to a rapid appearance of MDP in the blood and lungs, whereas parenteral administration is followed by a rise in MDP concentration 24 hours later.

Homogenates of mouse lung, liver and small intestine incubated with 1 mg/ml of WR 2721 converted all of the compound to MDP within 30 minutes; thus, demonstrating in vivo conversion of WR 2721 to its active free thiol derivative, for the reduction of mucin viscosity.

The administration of compounds containing protected sulfhydryl groups may be used in the treatment of any condition wherein excessive mucin viscosity is present. Such conditions include cystic fibrosis, pneumonia, bronchitis, the common cold, mucin impaction of gastrointestinal tract, pancreas, liver, and the like.

What is claimed as new and intended to be covered by Letters Patent is:

1. A method for reducing mucin viscosity in humans which comprises administering to said human effective a pharmaceutically effective dose of one or more compounds having protected sulfhydryl groups which metabolize in vivo to produce free sulfhydryl groups.

2. The method of claim 1, wherein the compound containing protected sulfhydryl groups is selected from the group consisting of:

$(H_2NCOCH_2CH_2NHCH_2CH_2S-)_2$
$H_2NCOCH_2CH_2NHCH_2CH_2SSO_3H$
$H_2NCOCH_2CH_2NHCH_2CH_2SPO_3H_2$
$H_2N(CH_2)_3NHCH_2CH_2SSO_3H$
$(H_2N(CH_2)_3NHCH_2CH_2S-)_2$
$CH_3(CH_2)_9NHCH_2CH_2SSO_3H$
$CH_3(CH_2)_9NHCH_2CH_2SPO_3H_2$
$(CH_3(CH_2)_9NHCH_2CH_2S-)_2$
$H_2NCH_2CH_2SPO_3H_2$
$H_2N(CH_2)_5NH(CH_2)_2SPO_3H_2$
$H_2N(CH_2)_3NH(CH_2)SPO_3H_2$ and their pharmaceutically acceptable salts.

3. The method of claims 1 or 2, wherein the effective dose is from 1 to 100 mg/kg/day.

4. The method of claim 3, wherein said effective dose is from about 5 to about 30 mg/kg/day.

5. The method of claim 1, wherein said compound containing protected sulfhydryl group has the formula: H₂N(CH₂)₃NH(CH₂)SPO₃H₂.

6. A method for reducing mucin viscosity in humans which comprises administering to said human a pharmaceutically effective dose of at least one compound selected from the group consisting of:

H₂NCOCH₂CH₂NHCH₂CH₂SPO₃H₂
CH₃(CH₂)₉NHCH₂CH₂SPO₃H₂
H₂NCH₂CH₂SPO₃H₂
H₂N(CH₂)₅NH(CH₂)₂SPO₃H₂
H₂N(CH₂)₃NH(CH₂)SPO₃H₂ and their pharmaceutically acceptable salts.

7. A method for reducing mucin viscosity in mammals which comprises administering to said mammal a pharmaceutically effective dose of at least one compound having a protective sulfhydryl group which metabolizes in vivo to produce free sulfhydryl groups and which is selected from the group consisting of thiosulfates, thiophosphates, and disulfides.

8. The method of claim 7, wherein said compounds are selected from the group consisting of aminoalkylthiosulfuric acids, aminoalkylphosphorothioates, thiosulfatoalkylamines, phenalkylaminoalkylthiosulfuric acids, hydroxyalkylaminoalkylthiosulfuric acids, hydroxyaminoalkylphosphorothioates, alkoxyalkylaminoalkylthiosulfuric acids, cycloalkyloxyaminoalkylthiosulfuric acids, phenoxyalkylaminoalkylthiosulfuric acids, cycloalkylaminoalkylthiosulfuric acids, cycloalkylalkylaminoalkylphosphorothioates, cycloalkylalkylaminoalkyldisulfides, phenoxyalkylaminoethyldisulfides, hydroxyalkylaminoalkyldisulfides, alkylamidiniumthiosulfates, acetamidine derivatives containing a blocked sulfhydryl group, arylalkylamidiniumthiosulfates, aminoalkylaminoalkylphosphorothioates, quinolyloxyalkylaminoalkylthiosulfuric acids, pyridyloxyalkylaminoalkylthiosulfuric acids, phenoxy- and phenylthioalkylamidiniumthiosulfates and cycloalkylamidiniumthiosulfates.

* * * * *